(12) United States Patent
Kim

(10) Patent No.: US 10,132,801 B2
(45) Date of Patent: Nov. 20, 2018

(54) METHOD FOR SCREENING NEW DRUG CANDIDATE INHIBITING TARGET PROTEIN-PROTEIN INTERACTION FOR DEVELOPMENT OF FIRST-IN-CLASS DRUG

(75) Inventor: So Youn Kim, Seoul (KR)

(73) Assignee: DONGGUK UNIVERSITY INDUSTRY-ACADEMIC COOPERATION FOUNDATION, Seoul (KR)

( * ) Notice: Subject to any disclaimer, the term of this patent is extended or adjusted under 35 U.S.C. 154(b) by 1131 days.

(21) Appl. No.: 13/322,651

(22) PCT Filed: May 28, 2010

(86) PCT No.: PCT/KR2010/003393
§ 371 (c)(1),
(2), (4) Date: Feb. 8, 2012

(87) PCT Pub. No.: WO2010/137903
PCT Pub. Date: Dec. 2, 2010

(65) Prior Publication Data
US 2012/0129722 A1 May 24, 2012

(30) Foreign Application Priority Data
May 28, 2009 (KR) ........................ 10-2009-0047136

(51) Int. Cl.
*C40B 20/02* (2006.01)
*C40B 30/04* (2006.01)
(Continued)

(52) U.S. Cl.
CPC ....... *G01N 33/54306* (2013.01); *C40B 20/02* (2013.01); *C40B 30/04* (2013.01); *G01N 33/6845* (2013.01)

(58) Field of Classification Search
CPC .. C40B 20/02; C40B 30/04; G01N 33/54306; G01N 33/6845
See application file for complete search history.

(56) References Cited

U.S. PATENT DOCUMENTS
2006/0121474 A1  6/2006  Kim et al.
2008/0318216 A1  12/2008  Giordano et al.
(Continued)

FOREIGN PATENT DOCUMENTS
KR   1020050056517 A   6/2005

OTHER PUBLICATIONS
Kim et al. (Anal. Chem., 2006, 78:7392-7396).*
(Continued)

*Primary Examiner* — Jeremy C Flinders
(74) *Attorney, Agent, or Firm* — Hultquist, PLLC; Steven J. Hultquist

(57) ABSTRACT

The present invention relates to a method for screening a substance inhibiting protein-protein interactions, and more particularly to a method for screening a substance inhibiting protein-protein interactions, the method comprising using a protein chip having immobilized thereon spots comprising a mixture of a sol-gel material and a protein. According to the invention, a protein chip can be easily manufactured in a 96-well plate using a sol-gel material, whereby an inhibitor that inhibits protein-protein interactions can be easily screened from a library of natural substances.

5 Claims, 10 Drawing Sheets
Specification includes a Sequence Listing.

(51) Int. Cl.
*G01N 33/68* (2006.01)
*G01N 33/543* (2006.01)
*C12N 15/09* (2006.01)

(56) References Cited

U.S. PATENT DOCUMENTS

2009/0227466 A1  9/2009  Kim
2010/0029507 A1  2/2010  Park et al.

OTHER PUBLICATIONS

Kelly et al. (J. Immunol., 1999, 163:5173-5177).*
Wang et al. (Trends in Pharmacological Sciences, 2008, 29(6):302-313).*
Koehn et al. (Nature Drug Discovery, 2005, 4:206-220).*
Lombardino, Joseph G., et al; "A guide to drug discovery: The role of the medicinal chemist in drug discovery—then and now," Nature Reviews Drug Discovery, Oct. 2004, pp. 853-862, vol. 3.
Wells, James A., et al., "Reaching for high-hanging fruit in drug discovery at protein-protein interfaces," Nature, 2007, pp. 1001-1009, vol. 450.
Kim, Soyoun, et al., "Improved sensitivity and physical properties of sol-gel protein chips using large-scale material screening and selection," Analytical Chemistry, 2006, pp. 7392-7396, vol. 78, Abstract only provided.
Chinese Office Action for Application No. 201080023581.0 dated Sep. 5, 2014.

\* cited by examiner

SEQUENCE LISTING

<160> NUMBER OF SEQ ID NOS: 10

<210> SEQ ID NO 1
<211> LENGTH: 789
<212> TYPE: DNA
<213> ORGANISM: Homo sapiens

<400> SEQUENCE: 1

```
atggagggag agaggaagaa caacaacaaa cggtggtatt tcactcgaga acagctggaa      60
aatagcccat cccgtcgttt tggcgtggac ccagataaag aactttctta tcgccagcag     120
gcggccaatc tgcttcagga catggggcag cgtcttaacg tctcacaatt gactatcaac     180
actgctatag tatacatgca tcgattctac atgattcagt ccttcacaca gttccctgga     240
aattctgtgg ctccagcagc cttgtttcta gcagctaaag tggaggagca gcccaaaaaa     300
ttggaacatg tcatcaaggt agcacatact tgtctccatc ctcaggaatc ccttcctgat     360
actagaagtg aggcttattt gcaacaagtt caagatctgg tcattttaga aagcataatt     420
ttgcagactt taggctttga actaacaatt gatcacccac atactcatgt agtaaagtgc     480
actcaacttg ttcgagcaag caaggactta gcacagactt cttacttcat ggcaaccaac     540
agcctgcatt tgaccacatt tagcctgcag tacacacctc ctgtggtggc ctgtgtctgc     600
attcacctgg cttgcaagtg gtccaattgg gagatcccag tctcaactga cgggaagcac     660
tggtgggagt atgttgacgc cactgtgacc ttggaacttt tagatgaact gacacatgag     720
tttctacaga ttttggagaa aactcccaac aggctcaaac gcatttggaa ttggagggca     780
tgcgaggct                                                            789
```

<210> SEQ ID NO 2

```
<211> LENGTH: 1119
<212> TYPE: DNA
<213> ORGANISM: Homo sapiens

<400> SEQUENCE: 2
atggcgaagc agtacgactc ggtggagtgc ccttttttgtg atgaagtttc caaatacgag      60
aagctcgcca agatcggcca aggcaccttc ggggaggtgt tcaaggccag gcaccgcaag     120
accggccaga aggtggctct gaagaaggtg ctgatggaaa cgagaaagga ggggttcccc     180
attacagcct tgcgggagat caagatcctt cagcttctaa acacgagaaa tgtggtcaac     240
ttgattgaga tttgtcgaac caaagcttcc ccctataacc gctgcaaggg tagtatatac     300
ctggtgttcg acttctgcga gcatgacctt gctgggctgt tgagcaatgt tttggtcaag     360
ttcacgctgt ctgagatcaa gagggtgatg cagatgctgc ttaacggcct ctactacatc     420
cacagaaaca agatcctgca tagggacatg aaggctgcta atgtgcttat cactcgtgat     480
ggggtcctga agctggcaga ctttgggctg gcccggggcct tcagcctggc caagaacagc     540
cagcccaacc gctacaccaa ccgtgtggtg acactctggt accggccccc ggagctgttg     600
ctcggggagc gggactacgg ccccccccatt gacctgtggg gtgctgggtg catcatggca     660
gagatgtgga cccgcagccc catcatgcag ggcaacacgg agcagcacca actcgccctc     720
atcagtcagc tctgcggctc catcaccccct gaggtgtggc caaacgtgga caactatgag     780
ctgtacgaaa agctggagct ggtcaagggc cagaagcgga aggtgaagga caggctgaag     840
gcctatgtgc gtgacccata cgcactggac ctcatcgaca agctgctggt gctggaccct     900
gcccagcgca tcgacagcga tgacgccctc aaccacgact tcttctggtc cgaccccatg     960
ccctccgacc tcaagggcat gctctccacc cacctgacgt ccatgttcga gtacttggca    1020
ccaccgcgcc ggaagggcag ccagatcacc cagcagtcca ccaaccagag tcgcaatccc    1080
gccaccacca accagacgga gtttgagcgc gtcttctga                           1119

<210> SEQ ID NO 3
<211> LENGTH: 26
<212> TYPE: DNA
<213> ORGANISM: Artificial Sequence
<220> FEATURE:
<223> OTHER INFORMATION: Synthetic Construct

<400> SEQUENCE: 3
gaattcatgg cgaagcagta cgactc                                          26

<210> SEQ ID NO 4
<211> LENGTH: 25
<212> TYPE: DNA
<213> ORGANISM: Artificial Sequence
<220> FEATURE:
<223> OTHER INFORMATION: Synthetic Construct

<400> SEQUENCE: 4
ctcgaggaag acgcgctcaa actcc                                           25

<210> SEQ ID NO 5
<211> LENGTH: 28
<212> TYPE: DNA
<213> ORGANISM: Artificial Sequence
<220> FEATURE:
<223> OTHER INFORMATION: Synthetic Construct

<400> SEQUENCE: 5
gaattcatgg agggagagag gaagaaca                                        28
```

```
<210> SEQ ID NO 6
<211> LENGTH: 25
<212> TYPE: DNA
<213> ORGANISM: Artificial Sequence
<220> FEATURE:
<223> OTHER INFORMATION: Synthetic Construct

<400> SEQUENCE: 6
gtcgacagcc tcgcatgccc tccaa                                              25

<210> SEQ ID NO 7
<211> LENGTH: 40
<212> TYPE: RNA
<213> ORGANISM: Artificial Sequence
<220> FEATURE:
<223> OTHER INFORMATION: Synthetic Construct

<400> SEQUENCE: 7
uuacagaaca accaacgucg cuccggguac uucuucaucg                              40

<210> SEQ ID NO 8
<211> LENGTH: 40
<212> TYPE: DNA
<213> ORGANISM: Artificial Sequence
<220> FEATURE:
<223> OTHER INFORMATION: Synthetic Construct

<400> SEQUENCE: 8
accatcgcgg aagtccagtc tgccatcaaa atccgaagtg                              40

<210> SEQ ID NO 9
<211> LENGTH: 40
<212> TYPE: DNA
<213> ORGANISM: Artificial Sequence
<220> FEATURE:
<223> OTHER INFORMATION: Synthetic Construct

<400> SEQUENCE: 9
aattctctct cttcataata ttccggcgtc tacatccact                              40

<210> SEQ ID NO 10
<211> LENGTH: 40
<212> TYPE: DNA
<213> ORGANISM: Artificial Sequence
<220> FEATURE:
<223> OTHER INFORMATION: Synthetic Construct

<400> SEQUENCE: 10
cacgcgttca acccccggaa tttagcaata gcagattacg                              40
```

METHOD FOR SCREENING NEW DRUG CANDIDATE INHIBITING TARGET PROTEIN-PROTEIN INTERACTION FOR DEVELOPMENT OF FIRST-IN-CLASS DRUG

CROSS-REFERENCE TO RELATED APPLICATIONS

This application is filed under the provisions of 35 U.S.C. § 371 and claims the priority of International Patent Application No. PCT/KR2010/003393 filed on 28 May 2010 entitled "Method for Screening New Drug Candidate Inhibiting Target Protein-Protein Interaction for Development of First-In-Class Drug" in the name of So Youn KIM, which claims priority of Korean Patent Application No. 10-2009-0047136 filed on 28 May 2009, both of which are hereby incorporated by reference herein in their entirety.

TECHNICAL FIELD

The present invention relates to a method for screening a substance inhibiting protein-protein interactions, and more particularly to a method for screening a substance inhibiting protein-protein interactions, the method comprising using a protein chip having immobilized thereon spots comprising a mixture of a sol-gel material and a protein.

BACKGROUND ART

It is known that there are many problems in the development of low-molecular-weight inhibitors that inhibit protein-protein interactions, but because of their importance, attempts have been continuously made to develop lower-molecular-weight substances that inhibits protein-protein interactions, and several successful examples have been reported (*Nature Reviews Drug Discovery*, 3:853, 2004). Methods for developing new drugs generally comprise constructing a specific assay system and performing high-throughput screening of a library of several ten to several million compounds using the assay system. These methods have been applied mainly in multinational pharmaceutical companies because of various limitations such as the amount of compounds to be analyzed or the construction of high-speed screening systems and were difficult to apply in small-scale laboratories. In order to construct a new high-throughput screening system for screening a relatively small-sized library of tens of thousands of compounds, such as a library of natural substances, there is a need to prove the concept at low costs within a short time. Also, in the case of small and medium-scale laboratories such as schools and institutes, a strategy that obtains lead compounds using new conceptual assay systems and screening systems is required.

Thus, it is required to establish new drug-screening methods using previously constructed chip systems made of inexpensive polymers, which are suitable for chip-based screening which can be applied to a small number of samples, thereby ensuring original technology. This will contribute to enhancing the infrastructure of the new drug development industry.

Accordingly, the present inventors have made extensive efforts to a chip-based method for screening inhibitors of protein-protein interactions, which can be advantageously used even in laboratory-based, small-scale experimentation. As a result, the present inventors have found that the use of a protein chip spotted with a mixture of a sol-gel material and a protein enables a protein-protein interaction inhibitor to be easily screened using an existing antibody assay method, thereby completing the present invention.

DISCLOSURE OF INVENTION

It is an object of the present invention to provide a chip-based method of screening a substance that inhibits protein-protein interactions, in which protein-protein interactions can be analyzed in a simple and easy way.

To achieve the above object, the present invention provides a method for screening a substance that inhibits protein-protein interactions, the method comprising the steps of: (a) manufacturing a protein chip having immobilized thereon spots comprising a mixture of a sol-gel material and a protein; (b) allowing the protein chip to react with a protein, which has the ability to bind to the protein immobilized on the chip, in the presence of a candidate substance that inhibits the binding between the proteins; and (c) measuring the binding between the protein immobilized on the chip and the protein having the ability to bind to the immobilized protein, and selecting the candidate substance as a substance inhibiting protein-protein interactions, if the binding between the proteins was determined to be inhibited compared to a case in which the candidate substance is not present.

Other features and embodiments of the present invention will be more apparent from the following detailed descriptions and the appended claims.

BEST MODE FOR CARRYING OUT THE INVENTION

Figure 1:
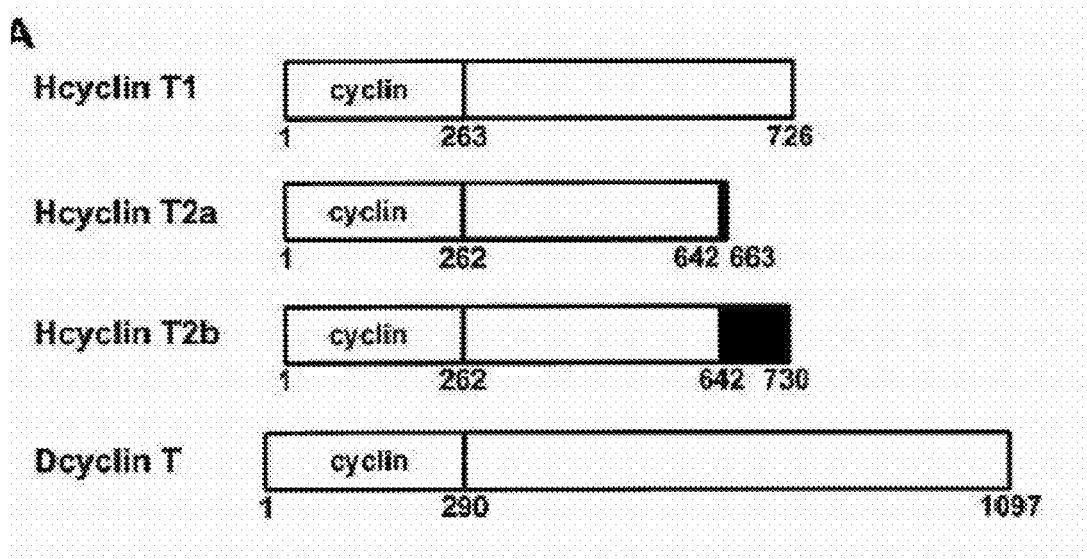
FIG. 1 shows the structural homology between Cyclin T proteins.

Unless defined otherwise, all technical and scientific terms used herein have the same meaning as commonly understood by one of ordinary skill in the art to which the invention pertains. Generally, the nomenclature used herein and the experiment methods which will be described later are those well known and commonly employed in the art.

In one aspect, the present invention is directed to a method for screening a substance that inhibits protein-protein interactions, the method comprising the steps of: (a) manufacturing a protein chip having immobilized thereon spots comprising a mixture of a sol-gel material and a protein; (b) allowing the protein chip to react with a protein, which has the ability to bind to the protein immobilized on the chip, in the presence of a candidate substance that inhibits the binding between the proteins; and (c) measuring the binding between the protein immobilized on the chip and the protein having the ability to bind to the immobilized protein, and selecting the candidate substance as a substance inhibiting protein-protein interactions, if the binding between the proteins was determined to be inhibited compared to a case in which the candidate substance is not present.

In the present invention, the candidate substance is preferably selected from the group consisting of natural substances, compounds and aptamers. In step (c) of the screening method according to the present invention, the binding between the proteins is preferably analyzed using an antibody against the protein having the ability to bind to the protein immobilized on the protein chip.

In the present invention, the spots are preferably immobilized on a 96-well plate. In the present invention, the protein immobilized on the protein chip is preferably CyclinT1, and the protein having the ability to bind to the protein immobilized on the protein chip is preferably CDK9.

In the present invention, in step (c) of selecting the candidate substance as the substance inhibiting protein-protein interactions, the candidate substance is selected as the inhibitory substance if the candidate substance did bind to the protein immobilized on the chip to inhibit the binding between the protein immobilized on the protein chip and the protein having the ability to bind to the immobilized protein.

For example, CyclinT1 is a protein interacting with CDK9. If a candidate substance binds to Cyclin T1 to inhibit the binding between CDK9 and CyclinT1 when the candidate substance and CDK9 were allowed to react with each other on a protein chip having Cyclin T1 immobilized thereon, the candidate substance can be selected as a substance inhibiting the interaction between Cyclin T1 and CDK9. Herein, the inhibition of the interaction may be analyzed by treating the protein chip with an antibody against CDK9, followed by treatment with secondary antibody, labeled with a fluorescent material (e.g., Cy3), against the CDK9 antibody. In other words, if the CDK9 antibody signal upon treatment with the candidate substance decreases compared to a case in which the candidate substance is not present, the candidate substance can be selected as a substance that inhibits the CyclinT1-CDK9 interaction.

In the present invention, the sol-gel substance preferably comprises 17.5 parts by weight of TMOS, 5-15 parts by weight of MTMS and 0-15 parts by weight of GPTMOS.

In the present invention, in order to establish new drug screening technology and verify a candidate group screened therefrom to discover a novel natural substance that inhibits protein-protein interactions, a chip-based screening system for screening a substance inhibiting protein-protein interactions was constructed.

Figure 5:
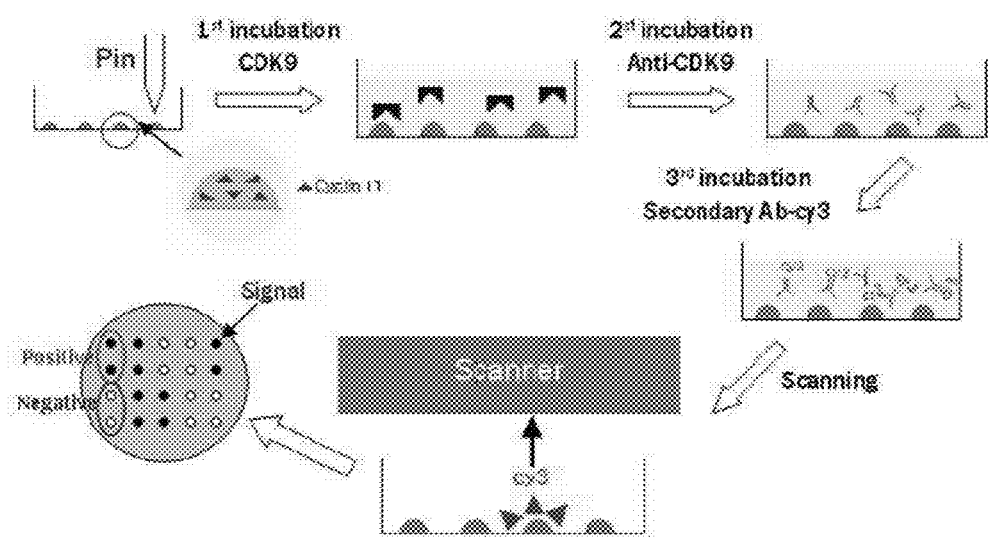
FIG. 5 is a schematic diagram showing a method of determining an interaction between CDK9 and Human Cyclin T1 on a sol-gel chip.

In one Example of the present invention, a chip-based system capable of analyzing CyclinT/Cdk9 interaction was established, thereby screening a CyclinT/Cdk9 inhibitor candidate. Specifically, as shown in FIG. 5, a mixture of a sol-gel material and CyclinT protein was spotted on a substrate to manufacture a protein chip. The protein chip was allowed to react not only with a CyclinT/Cdk9 interaction inhibitor candidate, such as a Actinomyces culture extract, a fungal culture extract, a plant extract or an aptamer, but also Cdk9, and then allowed to react sequentially with Cdk9 antibody and Cy3-labeled secondary antibody. Then, the chip was scanned, and whether a signal appeared in the spots was analyzed. The substance that was allowed to react in the spot showing no signal was determined to be an inhibitor substance.

EXAMPLES

Hereinafter, the present invention will be described in further detail with reference to examples. It will be obvious to those skilled in the art that these examples are illustrative purposes only and are not to be construed to limit the scope of the present invention.

Example 1: Cloning of Cyclin T Gene and CDK9 Gene and Purification of Cyclin T and CDK9

Cyclin T proteins are highly homologous proteins which contain a conserved region, called the "cyclin box" known to bind to CDK9. The cyclin box of human cyclin T (GenBank #NM_001240) consists of 266 amino acids and is represented by a nucleotide sequence of SEQ ID NO: 1 (FIG. 1). Human CDK9 (GenBank #BC001968) is shown in SEQ ID NO: 2.

As a template for amplifying CDK9 by PCR, a human cDNA mixture was used, and as a template for amplifying human Cyclin T1 by PCR, a 1:1 mixture of HEK293 cells and HeLa cells was used.

In the PCR amplification, the following primers were used:

SEQ ID NO 3:     GAATTCATGGCGAAGCAGTACGACTC
(human CDK9 forward primer; containing an EcoRI site);

SEQ ID NO: 4:    CTCGAGGAAGACGCGCTCAAACTCC
(human CDK9 reverse primer; containing an XhoI site);

SEQ ID NO: 5:    GAATTCATGGAGGGAGAGAGGAAGAACA
(human Cyclin T1 forward primer; containing an EcoRI site);

SEQ ID NO: 6:    GTCGACAGCCTCGCATGCCCTCCAA
(human Cyclin T1 reverse primer; containing a SalI site).

Each of the human CDK9 and human Cyclin T1 genes were amplified, TA-cloned by ligation into a T vector (Promega, USA), and then transformed into *E. coli* DH5α. Plasmids were purified from the transformed colonies, and the cloned genes were confirmed by electrophoresis and sequenced to determine the nucleotide sequences. Each of the cloned genes was cloned into a pET28a vector (Novagen, USA) which was then transformed into *E. coli* BL21 cells.

Figure 2:
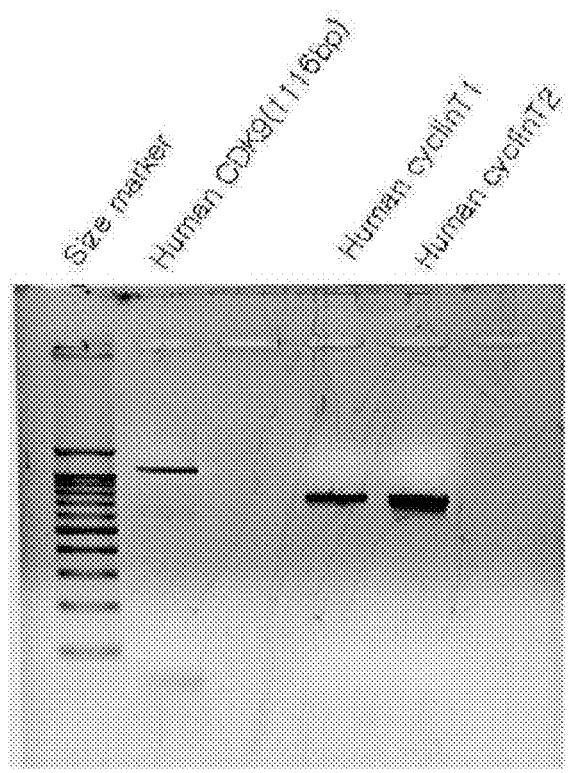
FIG. 2 shows the results of SDS-PAGE carried out to measure the expressions of recombinant CDK9 and Cyclin T in *E. coli* BL21.

The *E. coli* BL21 cells transformed with each of the human CDK9 gene and the human Cyclin T1 gene were cultured, and the expression of each of the genes in the cells was induced with IPTG, after which the bacterial cells were cultured additionally and collected. The expression of each of the proteins in the cells was analyzed by SDS-PAGE (FIG. 2).

Figure 3:
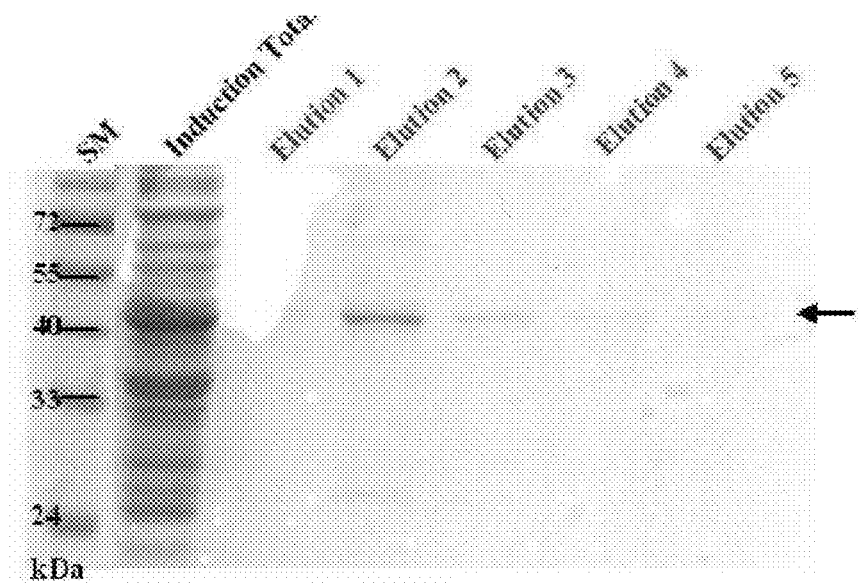
FIG. 3 shows the expression pattern of recombinant human CDK9 and a purification process thereof.
Figure 4:
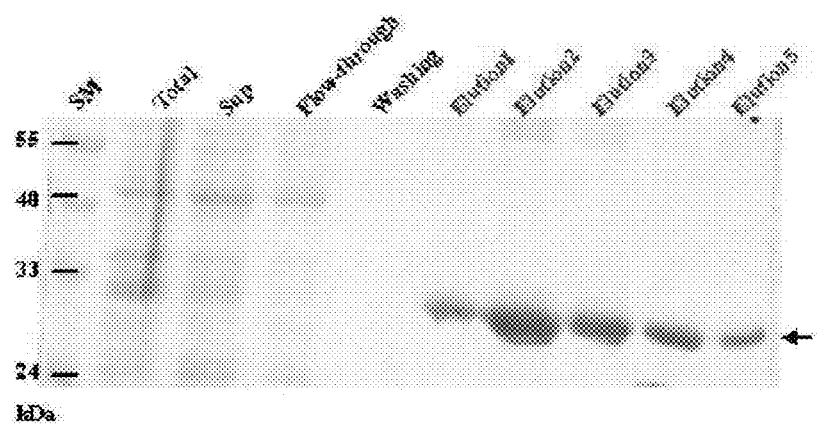
FIG. 4 shows the expression pattern of recombinant human cyclin T and a purification process thereof.

Each of the bacterial cell lines was added to and suspended in 10 mL of His-tag binding buffer containing PMSF and was lysed by sonication. Each of the cell lyses was applied to His tag resin to purify each of the human CDK9 gene and the human Cyclin T1, and SDS-PAGE was performed to analyze whether the human CDK9 protein and the human Cyclin T1 protein were sufficiently expressed (FIGS. 3 and 4).

Example 2: Analysis of Interaction Between Protein and Inhibitor on Chip

In order to analyze the interaction between CDK9 and human Cyclin T1 on a sol-gel chip, the binding between the proteins was analyzed on the chip by the method shown in FIG. 5.

50 ng of each of human Cyclin T1 and CDK9 was mixed with sol-gel material composition 1 (25.0% TMOS, 7.5% MTMS, and 5% GPTMOS) and spotted and immobilized on a 96-well plate by an arrayer. In order to prevent a substance having no affinity from adhering to the chip, the plate was blocked with skim milk-containing binding buffer, and then allowed to react with a 1:500 dilution of anti-CDK9 antibody binding to CDK9, at room temperature for 1 hour. In order to examine a signal in a scanner, the plate was allowed to react with a 1:1000 dilution of cy3-labelled secondary antibody at room temperature for 1 hour, after which the plate was scanned to analyze the signal of each protein (FIG. 6).

Figure 6:
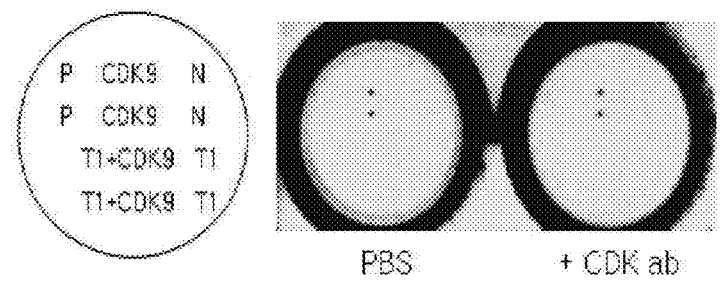
FIG. 6 shows the results of analyzing protein-protein binding on a sol-gel chip.

As a result, as can be seen in FIG. 6, a weak signal indicating the binding between CDK9 and anti-CDK9 appeared.

Before a library of natural substances was regularly screened, four natural substances were selected and the conditions of a chip-based assay system were established. Because the signal of CDK9 was weak as can be seen from the above results, 150 ng (three times 50 ng used above) of each of human Cyclin T1 and CDK9 was mixed with sol-gel material composition 2 (25.0% TMOS, 7.5% MTMS, and 15% GPTMOS) and immobilized on a 96-well plate.

The plate was blocked with skim milk-containing binding buffer, after which it was allowed to react with CDK9 (50 ng/rxn vol. 50 μl), followed by washing. Then, the plate was allowed to react with a 1:500 dilution of anti-CDK9 antibody at room temperature for 1 hour and washed, after it was allowed to react with 1:1000 dilution of cy3-labeled secondary antibody at room temperature for 1 hour and washed. Then, the plate was scanned, and the signal of each protein was analyzed.

Figure 7:
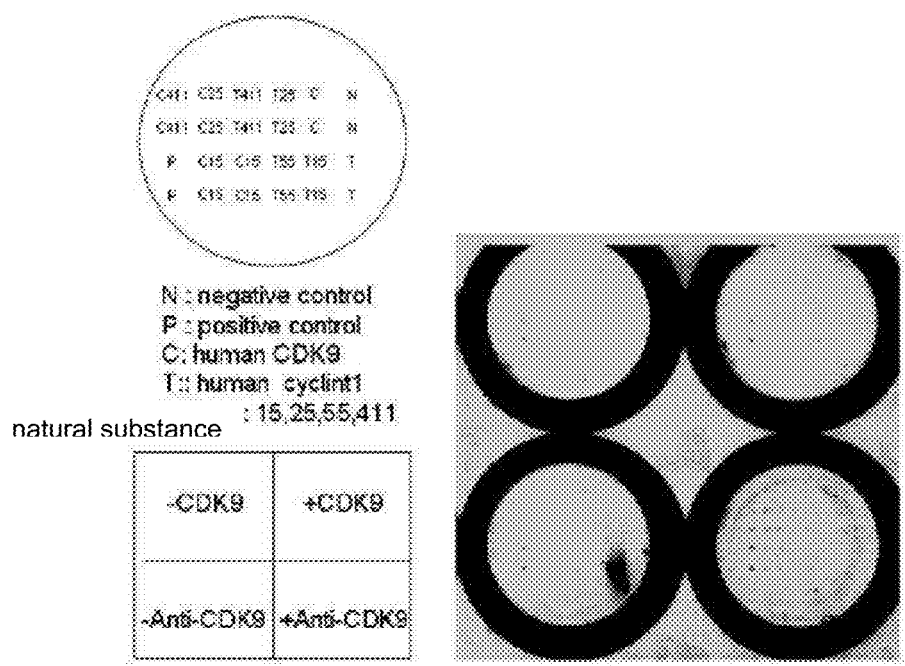
FIG. 7 shows the results of a preliminary test carried out using 4 natural substances on a sol-gel chip.

As a result, as can be seen in FIG. 7, the signal of the CDK9 spot appeared in the well in which the anti-CDK9 antibody alone was allowed to react, whereas no signal appeared in the well in which CDK9 and anti-CDK9 were allowed to react. For this reason, before screening a library of natural substances, a test for analyzing the binding between CDK9 and human Cyclin T1 on the chip was first performed.

180 ng of human Cyclin T1 and 150 ng of CDK9 were mixed with sol-gel material composition 1 (25.0% TMOS, 7.5% MTMS, and 5% GPTMOS) and spotted on a 96-well plate. Then, the plate was blocked with skim milk-containing binding buffer, after which it was allowed to react with CDK9 (50 ng/rxn vol. 50 μl) and washed. Then, the plate was allowed to react with a 1:500 dilution of anti-CDK9 antibody at room temperature for 1 hour and washed, after which it was allowed to react with 1:1000 dilution of cy3-labeled secondary antibody at room temperature for 1 hour and washed. Then, the plate was scanned, and the signal of each protein was analyzed.

Figure 8:
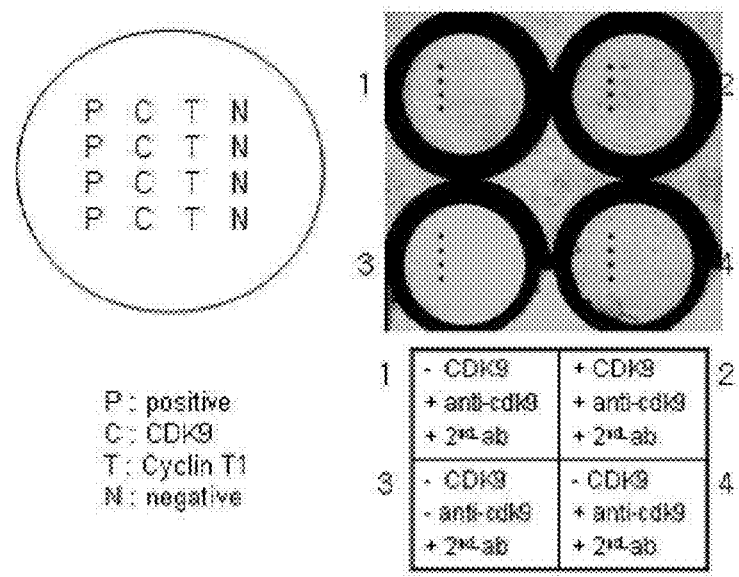
FIG. 8 shows the results of a test carried out to establish analysis conditions on a sol-gel chip.

As a result, as can be seen in FIG. 8, a signal appeared not only in well No. 2 in which both CDK9 and anti-CDK9 were allowed to react, but also in a negative spot immobilized with nothing, whereas little or no signal appeared in well Nos. 1 and 4 in which anti-CDK9 and secondary antibody were allowed to react. When the same test was repeated, no signal appeared in all the spots excluding a positive spot.

Based on the results of the above two tests and the results in FIG. 4, it was concluded that the test results were not constant because the composition of the sol-gel material was not suitable for the proteins. For this reason, a suitable sol-gel material composition was first selected. Because the signal appeared in the negative spot, it was believed that the plate was not sufficiently blocked, and thus the blocking time was increased from 1 hour to 2 hours in subsequent tests.

Example 3: Selection of Sol-Gel Material

Figure 9:
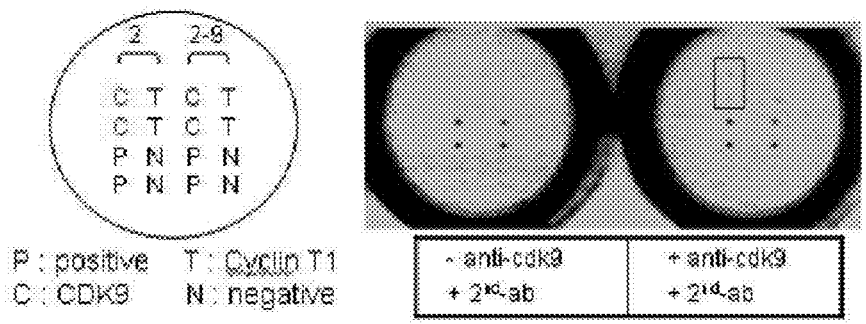
FIG. 9 shows the results of analysis according to the composition of a sol-gel material.

In order to select a sol-gel material suitable for immobilizing and assaying the protein, two sol materials having composition 1 (25.0% TMOS, 7.5% MTMS, and 5% GPTMOS) used in Example 2 and composition 2 (25.0% TMOS, 7.5% MTMS, and 15% GPTMOS) (which has a larger pore size than composition 2-9 and is thus advantageous for assaying large molecules), respectively, were immobilized with each of CDK9 (150 ng/11 μl sol-gel material), human Cyclin T1 (180 ng/11 μl sol-gel material), a positive control and a negative control, as shown in FIG. 9. Then, in the same manner as Example 2, each of the sol-gel materials was treated with the antibodies and scanned.

As a result, as can be seen in FIG. 9, it was shown in composition 2 that CDK9 and anti-CDK9 did bind to each other to show a signal and that anti-CDK9 did not bind to human Cyclin T1. For this reason, sol-gel material composition 2 was used in subsequent Examples.

Also, the sol-gel chip was allowed to react with CDK9 in order to examine whether CDK9 could bind to human Cyclin T1 on the chip. The sol-gel chip as shown in FIG. 9 was blocked with skim milk buffer, after which it was allowed to react with CDK9 (60 ng/rxn vol. 60 μl) and washed. Then, it was allowed to react with a 1:500 dilution of anti-CDK9 antibody binding to CDK9, at room temperature for 1 hour, followed by washing. Then, it was allowed to react with a 1:1000 dilution of Cy3-labeled secondary antibody at room temperature for 1 hour and scanned.

Figure 10:
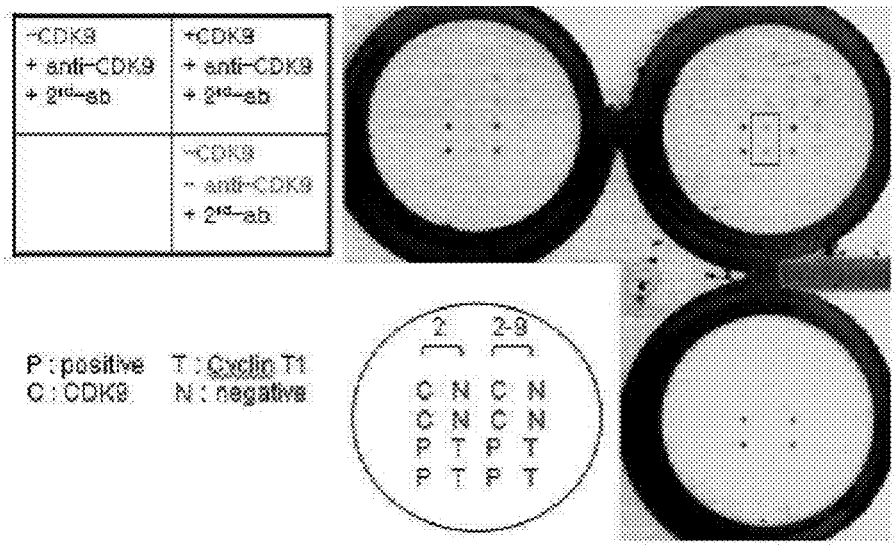
FIG. 10 shows the results of analysis according to the composition of a sol-gel material.

As a result, as can be seen in FIG. 10, in composition 1, a signal appeared even in the negative spot, whereas, in composition 2, a signal could be seen in the spot in which human Cyclin T1 and CDK9 did bind to each other. In addition, in the well in which CDK9 was not allowed to react, anti-CDK9 did not bind to human Cyclin T1.

From the above results, it was found that composition 1 was suitable for analyzing the protein-protein interaction. Also, the binding between CDK9 and human Cyclin T1 on the chip was confirmed using the chip-based assay system.

Example 4: Screening of Library of Natural Substances Using Chip-Based Assay System Using the chip-based assay system for protein-protein interactions established in Examples 2 and 3, a library of natural substances was screened. The library of natural substances contained 21 Actinomyces culture extracts, 40 fungal culture extracts and 19 plant extracts, which were obtained from the Korea Research Institute of Bioscience and Biotechnology. Each of the Actinomyces culture extracts were dissolved in a 1:1 solvent of acetone and water, and each of the plant extracts were dissolved in water at a concentration of 5 mg/mL.

First, Actinomyces culture extract #15, fungal culture extract (medium A) #25, fungal culture extract (medium B) #55 and plant extract #411 were selected and applied to a chip-based assay. 1 µl of a 1:100 dilution of each of the natural substance extracts and 150 ng of each of human Cyclin T1 and CDK9 (control) were mixed with sol-gel material composition 2 to make a volume of 11 µl. Then, each of the mixtures was immobilized on a 96-well plate.

The plate was blocked with skim milk buffer, after which it was allowed to react with CDK9 (60 ng/rxn vol. 60 µl) and washed. Then, the plate was allowed to react with a 1:500 dilution of anti-CDK9 antibody binding to CDK9, at room temperature for 1 hour, followed by washing. Then, the plate was allowed to react with 1:1000 dilution of cy3-labeled secondary antibody at room temperature for 1 hour.

Figure 11:
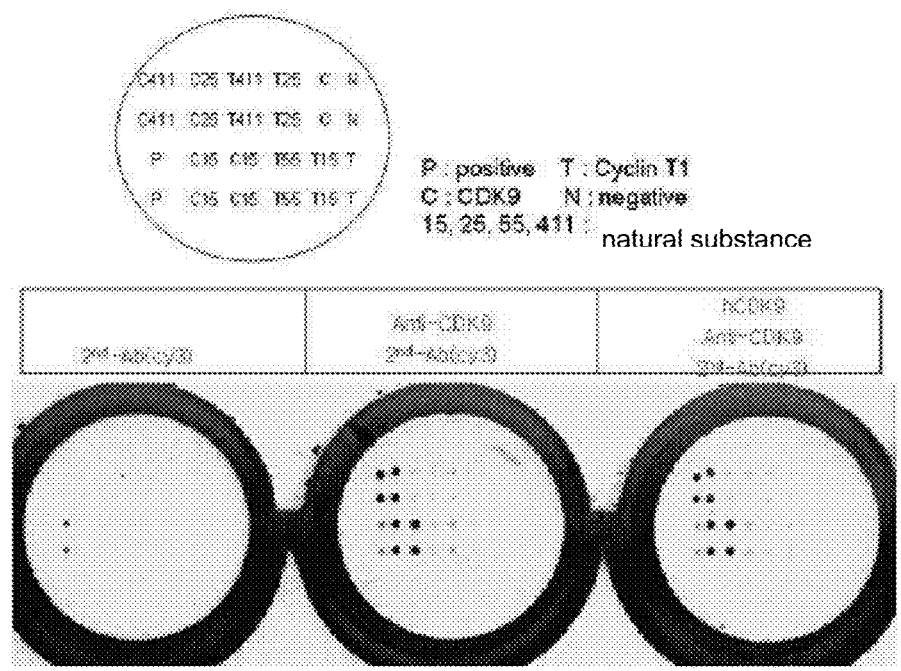
FIG. 11 shows the results of analyzing the effect of a library of natural substances on the inhibition of the interaction between CDK9 and human Cyclin T1.

As a result, as can be seen in FIG. 11, the signal of human Cyclin T1 appeared even in the well in which CDK9 was not allowed to react, but this signal was believed to be a background that looked like a signal because the sol-gel spot was scanned after drying for an excessively long time. For this reason, the spots were scanned after drying for a constant time.

Example 5: Improvement of Sol-Gel Material of Chip-Based Assay System

In order to change the formulation of sol-gel to find a composition at which the interaction between CDK9 and CyclinT1 can most easily occur, the composition of three silicate monomers and buffer in composition 1 was changed to prepare new compositions having a pore size different from that of composition 1.

In order to analyze protein-protein interactions in each of the compositions, BSA was mixed with a sol-gel material of each composition and spotted on a 96-well plate. Specifically, 500 ng/µl of BSA was mixed with a sol-gel material of each composition and spotted on a 96-well plate. In order to analyze a signal, the plate was allowed to react with a 1:500 dilution of Cy3-anti-BSA for 1 hour, after which it was washed and scanned.

Figure 12:
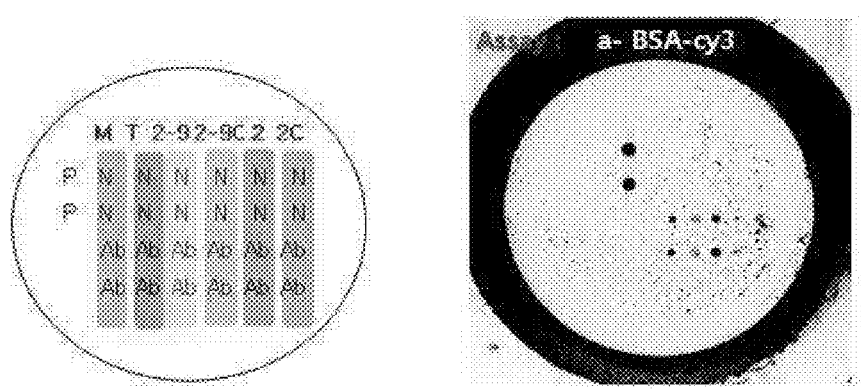
FIG. 12 shows the results of analyzing BSA signals according to the composition of a sol-gel material.

As a result, as can be seen in FIG. 12, the signal was more intense in composition T and composition 3 (25.0% TMOS, 7.5% MTMS, 0% and GPTMOS, 2-9C) than in original composition 1 (2-9), and sol-gel spots of the remaining compositions were detached from the well surface during analysis.

Figure 13:
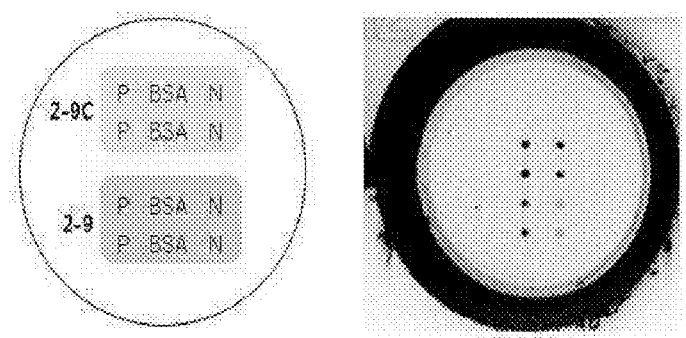
FIG. 13 shows the results of analyzing BSA signals according to the composition of a sol-gel material.

Composition 3 (2-9C) and composition 1 (2-9) were used to immobilize BSA and assayed in the same manner as above, after the signal of each signal was analyzed. As a result, it could be seen that the signal of composition 3 was clearer than the signal of composition 1 (FIG. 13).

Example 6: Screening of Natural Substances Using Chip-Based Assay

Figure 14:
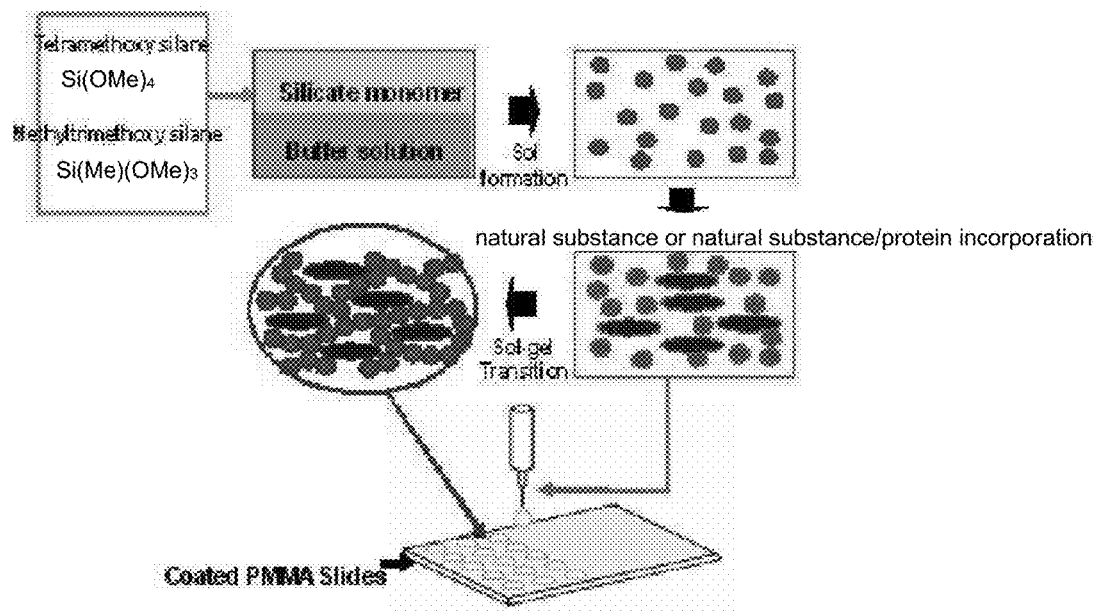
FIG. 14 shows a process of constructing a natural substance screening system for analyzing the inhibition of protein-protein interactions.
Figure 15:
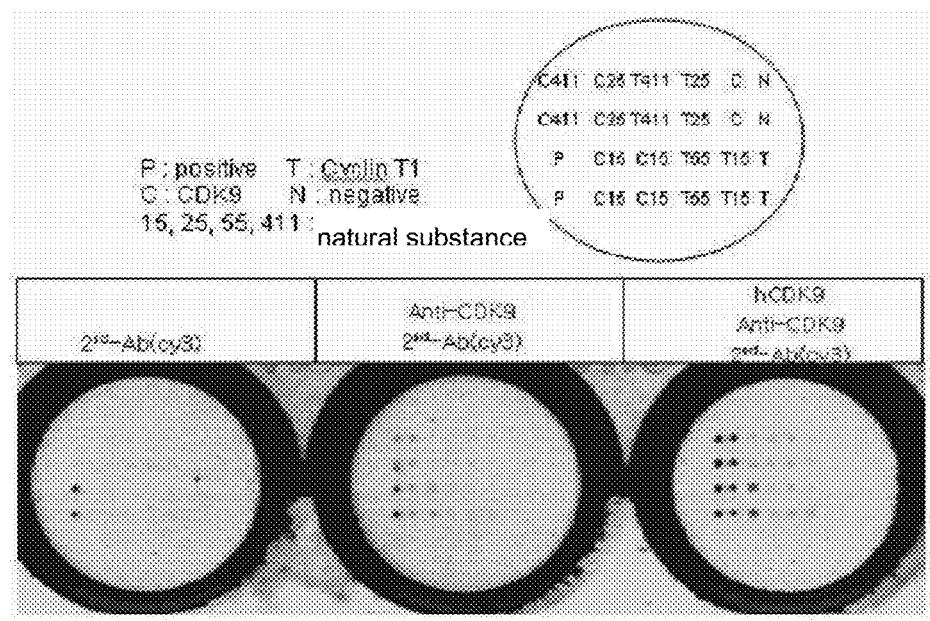
FIG. 15 shows the results of analyzing the effects of 3 natural substances on the inhibition of the interaction between DK9 and human Cyclin T1 on a low-density chip.

As shown in FIG. 14, a protein-protein interaction analysis system for full screening of natural substances was constructed using the composition confirmed in Example 5. Low-density chips were manufactured based on three selected natural substances and tested. As a result, as shown in FIG. 15, when only anti-CDK9 and secondary antibody were allowed to react to react, a signal appeared only in a spot in which CDK9 and a natural substance were immobilized, and when CDK9, anti-CDK9 and secondary antibody were allowed to react, a signal could appear in spots in which CDK9, a natural substance and human Cyclin T1 were immobilized, but the signal was observed to be weak.

Thus, it could be seen that, among the natural substances, Actinomyces culture extract #15, fungal culture extract (medium A) #25, fungal culture extract (medium B) #55 and plant extract #411 weakly acted on the binding between CDK9 and human Cyclin T1.

Example 7: Development of Nucleic Acid Marker Inhibiting Interaction Between CDK9 and Cyclin T1

In order to verify whether the chip-based system of the present invention can be used to develop inhibitors of protein-protein interactions, an aptamer were prepared and tested using the chip-based system.

Figure 16:
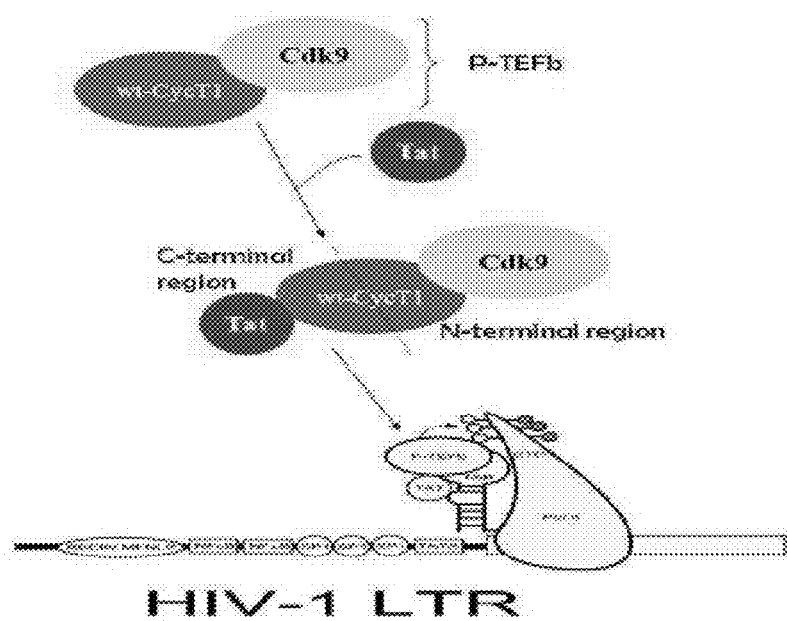
FIG. 16 is a schematic view showing the mechanism of interaction between CyclinT1 and CDK9.

When CDK9 and CyclinT1 bind to each other in vivo, Tat protein binds to the C terminal region of CyclinT1, and RNA polymerase binds thereto while cell division occurs (FIG. 16). A new protein was prepared by deleting the C-terminal region of the cyclin box of CyclinT binding to CdK9, and an RNA aptamer therefor was prepared using an SELEX method. The template used to prepare the aptamer was as follows:

```
Template:
GGTAATACGACTCACTATAGGGAGATACCAGCTTATTCAATT-N40-
AGATAGTAAGTGCAATCT
```

Specifically, a single strand having a 40-bp random sequence was prepared, amplified by PCR, and then subjected to reverse transcription, thereby preparing an RNA library having a complexity of $10^{15}$.

Using a filter binding assay technique, CyclinT1 was immobilized on a nitrocellulose membrane to which a protein is easily bind but DNA and RNA do not bind.

Figure 17:
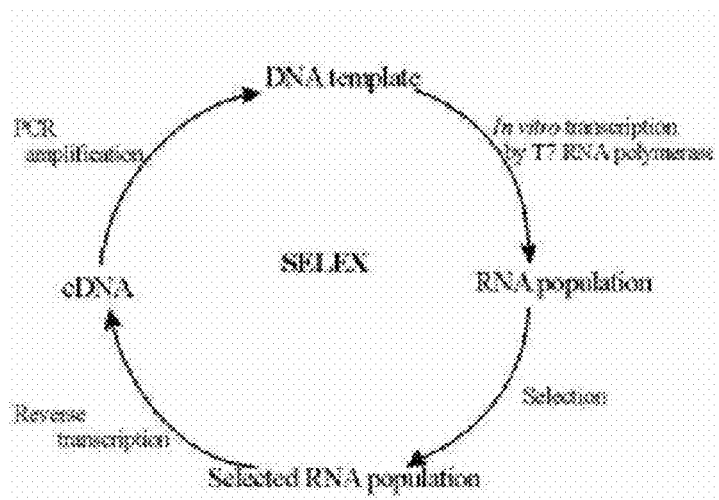
FIG. 17 is a schematic view showing an SELEX method for constructing a CyclinT1 aptamer.

Specifically, the RNA library and the target protein CyclinT were mixed at a ratio of 1:1 and allowed to react for 2 hours. Then, the reaction product was transferred to a nitrocellulose membrane and filtered, and RNA molecules which did not bind to the protein were washed out. The protein-RNA was eluted from the membrane and treated with PCI and then precipitated from ethanol, thereby obtaining RNA. The obtained RNA was amplified by PCR and subjected to reverse transcription, thereby preparing a new library to be assayed by SELEX. The above process was repeated 8 times, thereby obtaining an aptamer for Cyclin T (FIG. 17).

The aptamer was cloned into a TA cloning vector, after which colonies were collected therefrom and sequenced to determine the aptamer sequences (SEQ ID NOS: 7-10), and the secondary structures of the aptamers were determined.

The primers used herein were as follows:

```
SEQ ID NO 7:
UUACAGAACAACCAACGUCGCUCCGGGUACUUCUUCAUCG

SEQ ID NO 8:
ACCATCGCGGAAGTCCAGTCTGCCATCAAAATCCGAAGTG

SEQ ID NO: 9:
AATTCTCTCTCTTCATAATATTCCGGCGTCTACATCCACT

SEQ ID NO: 10:
CACGCGTTCAACCCCCGGAATTTAGCAATAGCAGATTACG
```

Figure 18:
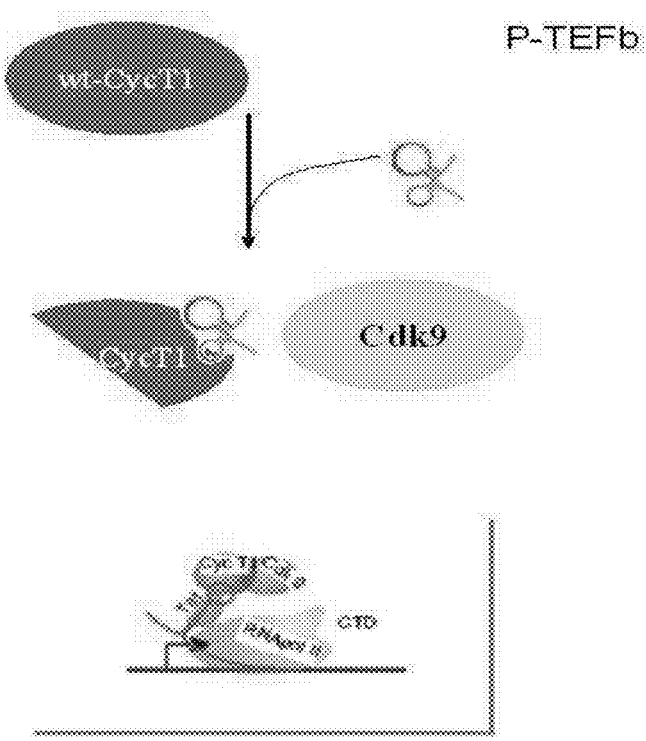
FIG. 18 is a schematic view showing the mechanism of action of a CyclinT1 aptamer.

It was expected that the aptamer would bind to the N-terminal region of CyclinI1 to inhibit the interaction between CyclinI1 and CDK9 so as to inhibit the binding of RNA polymerase, thereby inhibiting the proliferation of cells (FIG. 18).

Figure 19:
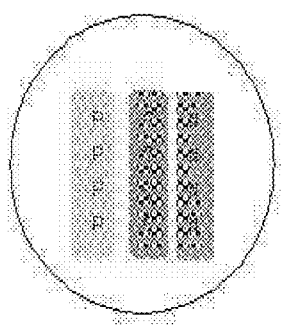
FIG. 19 shows the results of analyzing the binding between an aptamer and CyclinT1 on a sol-gel chip.
Figure 19:
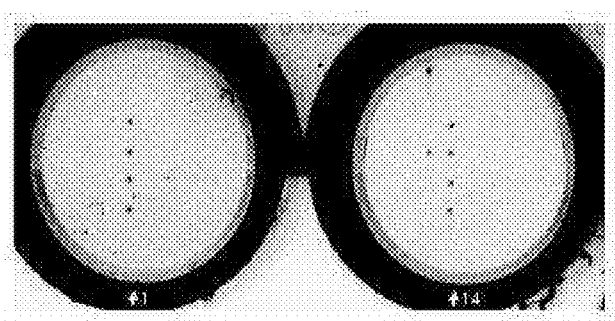

Using the sol gel 2-9C composition, CyclinT1 was immobilized, and the binding of CyclinT1 with the aptamer was analyzed. Specifically, each of four Cy3-labeled aptamers was allowed to react for 2 hours in wells in which CyclinT1 was immobilized. The reaction products were washed and scanned, thereby analyzing whether the aptamers the aptamers did bind to CyclinT1 (FIG. 19).

Specifically, CyclinT1 (1 mg/1 ml) was mixed with sol gel composition 3 and spotted on a 96-well plate, thereby manufacturing a chip having cyclinT1 immobilized thereon. Each well of the plate was allowed to react sequentially with CDK9, anti-CDK9 and Cy3-labeled secondary antibody, followed by washing.

As a result, in the well in which the aptamer which did not bind to CyclinT1 was allowed to react, CyclinT1 and CDK9 in the sol gel did bind to each other to show a signal, and in the well in which the aptamer bound to CyclinT1, no signal was observed.

Such results indicate that the chip-based screening system according to the present invention can be used to screen inhibitors of protein-protein interactions.

INDUSTRIAL APPLICABILITY

As described above, according to the present invention, a protein chip can be easily manufactured in a 96-well plate using a sol-gel material, whereby an inhibitor that inhibits protein-protein interactions can be easily screened from a library of natural substances.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A method for high-throughput screening a substance that inhibits protein-protein interactions, the method comprising the steps of: (a) manufacturing a protein chip comprising spots, wherein the spots are made by immobilizing mixtures comprising a sol-gel material, a first protein having the ability to bind to a second protein, and a plurality of candidate substances binding to the first protein, and each of the mixtures is immobilized on a well of the chip, wherein the candidate substances are natural substances or aptamers; (b) allowing the protein chip to react with the second protein, which has the ability to bind to the first protein immobilized on the chip; and (c) measuring the binding between the first protein immobilized on the chip and the second protein by analyzing a signal appeared in the spots, and selecting a candidate substance showing reduced or no signal in the spot based on the inhibition of the binding between the first protein and the second protein, relative to signal in the spot of the binding between the first protein and the second protein when the candidate substance is not present.

2. The method of claim 1, wherein the binding between the first protein and the second protein in step (c) is analyzed using an antibody against the second protein.

3. The method of claim 1, wherein the spots are immobilized on a 96-well plate.

4. The method of claim 1, wherein the first protein is CyclinT1, and the second protein is CDK9.

5. The method of claim 1, wherein the sol-gel substance comprises 17.5 parts by weight of TMOS, 5-15 parts by weight of MTMS and 0-15 parts by weight of GPTMOS.

\* \* \* \* \*

UNITED STATES PATENT AND TRADEMARK OFFICE
CERTIFICATE OF CORRECTION

PATENT NO. : 10,132,801 B2
APPLICATION NO. : 13/322651
DATED : November 20, 2018
INVENTOR(S) : So Youn Kim It is certified that error appears in the above-identified patent and that said Letters Patent is hereby corrected as shown below:

At page 2, item (56), under the heading, "OTHER PUBLICATIONS", in the identification of the Kim, et al. article (6th reference), at Lines 3-4 thereof, the wording ", Abstract only provided" is deleted.

Signed and Sealed this
Fifteenth Day of January, 2019

Andrei Iancu
*Director of the United States Patent and Trademark Office*